United States Patent [19]

Schweighardt

[11] Patent Number: 4,866,096
[45] Date of Patent: Sep. 12, 1989

[54] STABLE FLUOROCHEMICAL AQUEOUS EMULSIONS

[75] Inventor: Frank K. Schweighardt, Allentown, Pa.

[73] Assignee: Air Products and Chemicals, Inc., Allentown, Pa.

[21] Appl. No.: 28,522

[22] Filed: Mar. 20, 1987

[51] Int. Cl.$^4$ ............................................. A61K 31/025
[52] U.S. Cl. ..................... 514/756; 514/747; 514/786; 514/832; 514/937
[58] Field of Search ..................... 514/756, 832, 747

[56] References Cited

U.S. PATENT DOCUMENTS

| | | | |
|---|---|---|---|
| 3,776,857 | 12/1973 | Lindner | 252/308 |
| 3,962,439 | 6/1976 | Yokoyama et al. | 424/248 |
| 4,397,870 | 8/1983 | Sloviter | 424/325 |
| 4,423,077 | 12/1983 | Sloviter | 424/325 |
| 4,443,480 | 4/1984 | Clark, Jr. | 424/352 |
| 4,497,829 | 2/1985 | Sloviter | 514/672 |
| 4,533,254 | 8/1985 | Cook et al. | 366/176 |

FOREIGN PATENT DOCUMENTS 220153  4/1987  European Pat. Off. .
2091098 7/1982  United Kingdom .

OTHER PUBLICATIONS

L. C. Clark, Jr.-"Pathophysiology of Shock, Anoxia, and Aschemia", p. 507, Williams and Wilkins Publishers (1982).
Dr. Robert Geyer, "Synthesis and Biological Screening of New and Improved Fluorocarbon Compounds for Use as Artificial Blood Substitutes", Harvard University School of Public Health (RFP-NHLI-HB-75-19)
Edward M. Levine et al., Artificial Blood on the Laboratory Horizon (Lab World).
Jean G. Riess, "Reassessment of Criteria for the Selection of Perfluorochemicals for Second-Generation Blood Substitutes: Analysis of Structure/Property Relationships", published in Artificial Organs, 8(1):44-56 Raven Press, New York 1984.
Industrial and Engineering Chemistry, vol. 39, p. 380 (1949) Journal of Chemical Society, 1950, p. 3617 and Advance of Fluorine Chemistry, vol. I, p. 129, (1960).

*Primary Examiner*—Leonard Schenkman
*Attorney, Agent, or Firm*—Geoffrey L. Chase; James C. Simmons; William F. Marsh

[57] ABSTRACT

A stable aqueous emulsion of perfluorochemical, a phospholipid and a triglyceride of fatty acids has been demonstrated which has enhanced stability, diminished particle size and heightened tolerance by biological systems. The emulsion has utility as an oxygen transport medium, such as artificial blood.

14 Claims, No Drawings

STABLE FLUOROCHEMICAL AQUEOUS EMULSIONS

TECHNICAL FIELD

The present invention is directed to biologically acceptable oxygen transport media comprising aqueous emulsions of perfluorochemicals in complex emulsification systems. More specifically, the present invention is directed to an aqueous perfluorochemical emulsion having utility in the field of resuscitative fluids or artificial blood.

BACKGROUND OF THE PRIOR ART

It is generally known that some kinds of fluorocarbon emulsions have utility as blood substitutes, wherein the fluorocarbon acts as an oxygen transport medium in place of the hemaglobin function in natural blood of mammals.

Fluorocarbon emulsion particle size has been identified as a factor in toxicity and has adverse effects upon biological systems, such as test animals wherein particles having a size of 0.4 micron or average particle size of greater than 0.2 micron have been identified as problematic to effective maintenance of such test animals.

In light of the requirement for extremely small fluorocarbon particle size in stable emulsions for blood substitute or oxygen transport utility, difficulties in appropriate emulsification and stability under general storage conditions exist due to the incompatibility of the fluorocarbons and their aqueous medium in which they are emulsified.

Various fluorocarbons have been utilized for experimentation in the area of oxygen transport in mammals, including perfluorotripropylamine, perfluorodecalin, perfluoromethyldecalin and perfluorotributylamine.

Various emulsifiers have been utilized to emulsify fluorocarbons in an aqueous phase, including lipids, most notably lethicin from egg yolk phospholipids and soybean phospholipids and the monoglyceride of fatty acid selected from the group consisting of caprylic acid, capric acid, lauric acid, myristic acid, palmitic acid, stearic acid, behenic acid, palmitoleic acid, oleic acid, linolenic acid and arachidonic acid.

These fluorocarbons and emulsifiers are dispersed in aqueous media having physiological acceptance, including isotonic solutions such as Tyrode solution, Ringer's solution, lactated Ringer's solution or Ringer's solution containing glucose, and in some instances such aqueous media include emulsifier adjuvants, such as traces of fatty acid.

In U.S. Pat. No. 3,962,439, an artificial blood is set forth having a perfluorocarbon of 9-11 carbon atoms, a particle size of 0.05-0.3 microns and an emulsifier of a phospholipid and an emulsifying adjuvant of a fatty acid, its salt or the monoglyceride of such fatty acid. The fluorocarbon comprises a 10-40% weight to volume concentration in a phospholipid emulsion containing 2-6% weight/volume and minor amounts of fatty acid.

In U.S. Pat. No. 4,397,870 a process is set forth for the prolonged stability of perfluoro compounds in animals and humans comprising injecting an emulsifying agent into the perfused individual. The patent recites that the perfluoro compound represents 15-40% volume per volume of the total mixture which corresponds to 30-75 percent weight per volume and 7-9% weight per volume of lecithin.

U.S. Pat. No. 4,423,077 describes a stable emulsion of perfluoro compounds having a content of 30-75% weight per volume and a 7-9% weight per volume of a lipid which coats the perfluoro compound in a physiologically acceptable aqueous medium. The emulsion of this patent has a particle size of approximately 0.1 micron and 95% of the particles had diameters below 0.2 microns.

U.S. Pat. No. 4,497,829 is directed to stable emulsions prepared by dispersing a purified lipid in a physiologically acceptable aqueous medium by sonication, adding perfluoro compound to the dispersion, sonicating the mixture of lipid in perfluoro compound to form an emulsion of lipid-coated particles of perfluoro compound and centrifuging the emulsion formed to separate oversized particles.

The present invention provides an advance over the prior art of artificial blood media to provide decreased particle size, increased stability and longer shelf life for an oxygen transport media useful in mammals.

BRIEF SUMMARY OF THE INVENTION

The present invention represents a stable aqueous emulsion of a perfluorochemical comprising approximately 10-50 weight/volume percent perfluorochemical, approximately 0.5 up to 7 weight percent of a phospholipid which emulsifies said perfluorochemical and approximately 5-30 weight percent of a triglyceride of fatty acids with the remainder comprising an aqueous medium.

Preferably, the perfluorochemical is selected from the group consisting of perfluoroalkylcyclohexane having 3-5 carbon atoms in the alkyl radical, perfluorodecalin or perfluoromethyldecalin. Optimally, the perfluorocarbon is perfluorodecalin.

Alternatively the perfluorochemical is perfluorooctylbromide or perfluoroperhydrophenanthrene.

Preferably, the emulsion contains 20-40 weight/volume percent of the perfluorochemical. Preferably, the phospholipid is present in the range of 1-2 wt%. Preferably, the triglyceride of fatty acids is present in the range of 10-20 wt%.

Preferably, the phospholipid is an egg phosphatide. Preferably, the triglyceride of fatty acids is selected from the group consisting of safflower oil, soybean oil or mixtures thereof.

Optimally, the present invention consists of a stable emulsion in a physiologically acceptable aqueous medium of an oxygen-transferable saturated perfluorodecalin having essentially no detectable hydrogen or olefinic character and a mean particle size of about 0.15 microns which comprises said perfluorodecalin in a concentration of 10-50 weight/volume percent, a phospholipid as an emulsifier in a concentration of approximately 1.2 wt%, at least one triglyceride of fatty acids as an emulsifier adjuvant in a concentration of 10-20 wt% wherein the fatty acids have 16-18 carbon atoms, and glycerin in an amount of approximately 2.5 wt%, said emulsion being suitable for use as a blood substitute.

DETAILED DESCRIPTION OF THE INVENTION

In the present invention, various perfluorochemicals are known to be useful as oxygen transport components of mixtures of various biological systems. These perfluorochemicals are typically perfluorocarbons and can include among others three groups.

The first group of the perfluorocarbon compounds used in the invention is a perfluorocycloalkane or perfluoro(alkylcycloalkane) which includes, for example, perfluoro($C_{3-5}$-alkylcyclohexanes) such as perfluoro(methylpropylcyclohexanes), perfluoro(butylcyclohexanes), perfluoro(trimethylcyclohexanes), perfluoro(ethylpropylcyclohexanes) and perfluoro(pentylcyclohexanes); perfluorodecalin, perfluoro(methyldecalines) and perfluoroperhydrophenanthrene.

The second group is a perfluoro(alkylsaturated-heterocyclic compound) which includes, for example, perfluoro(alkyltetrahydropyrans) such as perfluoro(butyltetrahydropyrans), perfluoro(pentyltetrahydropyrans) and perfluoro(hexyltetrahydropyrans); perfluoro(alkyltetrahydrofurans) such as perfluoro(pentyltetrahydrofurans), perfluoro(hexyltetrahydrofurans) and perfluoro(heptyltetrahydrofurans); perfluoro(N-alkylpiperidines) such as perfluoro(N-pentylpiperidines), perfluoro(N-hexylpiperidines) and perfluoro(N-butylpiperidine); and perfluoro(N-alkylmorpholines) such as perfluoro(N-pentylmorpholines), perfluoro(N-hexylmorpholines) and perfluoro(N-heptylmorpholines).

The third group is a perfluoro(tert-amine) which includes, for examples, perfluorotripropylamine, perfluorotributylamine, perfluoro(diethylhexylamines), perfluoro(dipropylbutylamines) and perfluoro(diethylcyclohexylamines); and a perfluoro(dioxalkane), that is, perfluoro(alkylene glycol dialkyl ether), such as perfluoro(3,8-dioxa-2,9-dimethyldecane) or perfluoro(tetramethylene glycol diisopropyl ether), perfluoro(3,7-dioxa-2,8-dimethylnonane) or perfluoro(trimethylene glycol diisopropyl ether) and perfluoro(4,6-dioxa-5,5-dimethylnonane) or perfluoro(isopropylene glycol di-n-propyl ether).

The above groups are not inclusive, but rather the perfluorochemical can be selected from other compounds not recited herein, such as perfluorooctylbromide.

These perfluorochemical compounds are used alone or in a mixture of their isomers, and further of two or more kinds of the compounds. The compounds may be available on market. Alternatively, they may be produced according to the processes described, for example, in the articles of Industrial and Engineering Chemistry, Vol. 39, page 380 (1949), Journal of Chemical Society, 1950, page 3617, and Advance of Fluorine Chemistry, Vol. I, page 129 (1960) or by other fluorination techniques known in the art.

The root chemical compound may be essentially completely perfluorinated to remove all hydrogens and unsaturation by a multiple stage fluorination technique. The hydrocarbon is first subjected to fluorination using a $CoF_3$ particulate bed operated at a temperature of approximately 275°–427° C. The chemical compound is carried through the bed with a nitrogen carrier gas at a pressure of ambient up to 2 psig. The nitrogen to organic ratio is in the range of 10/90 to 90/10. Yields from this fluorination are typically 50 to 80% of theoretical. Alternatively, compounds from the third group above are fluorinated in a Simon Cell by well known technology.

The crude fluorochemical obtained from the cobalt trifluoride reactor can be reacted with elemental fluorine to remove trace amounts of residual hydrogen and unsaturation. Preferably the crude fluorochemical is subjected to a fluorine/nitrogen mixture containing 5–100% fluorine. The concentration and flow rate of the fluorine mixture is controlled to maintain temperatures below the boiling point of the fluorochemical. Depending upon the extent of fluorination in the cobalt trifluoride reactors, the direct fluorination is continued for a period of up to 36 hours or unit analysis indicates no detectable residual hydrogen or olefinic character.

As an alternative to direct fluorination, multiple passes through the cobalt trifluoride reactor have also been used to minimize residual hydrogen and olefinic character. This is the most commonly reported method.

In addition to the above techniques which convert residual contaminants to the desired product, other chemical extraction techniques have been used for the removal of trace contaminants to produce biocompatible fluorochemicals. A purification method whereby the fluorochemical is reacted with an aqueous alkaline solution in the presence of a secondary amine, has been used to remove residual hydrogen. See L. C. Clark, Jr., *Pathophysiology of Shock, Anoxia, and Aschemia*, page 507, Williams and Wilkins Publishers (1982).

Another method is to sequentially distill the fluorochemical from a slurry containing sodium fluoride, sodium hydroxide and potassium permanganate. See Dr. Robert Geyer, *Synthesis and Biological Screening of New Improved Fluorocarbon Compounds for Use as Artificial Blood Substitutes*, Harvard University School of Public Health (RFP-NHLI-HB-75-19.

The perfluorochemical is then subjected to distillation and filtration through successive beds of sodium fluoride, activated carbon and alumina to result in the ultrapure perfluorochemical compound preferred for biological applications of the subject emulsions compositions.

Among the perfluorochemicals compounds mentioned above, the most preferable ones are perfluorodecalin and perfluoro(methyldecalin) owing to their faster excretion from body, known biocompatibility, lack of retention in internal organs and their availability. The perfluorochemical is present in the emulsions of the present invention in the range of approximately 10 to 50 wt/vol percent, wherein that term is determined by dividing the grams of perfluorochemical by the total milliliters of resulting emulsion.

The phospholipid emulsifier is generally a naturally occurring and recovered lipid from egg yolk or soybean derivative. These phospholipids preferably comprise yolk lecithin or soybean lecithin, generally known as monoaminomonophosphatide compounds. The egg phosphatides are preferable.

Egg phosphatides, purified, are primarily a mixture of naturally occurring phospholipids which are isolated from egg yolk. These phospholipids have the following general structure:

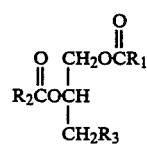

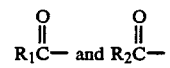

are the same saturated and unsaturated fatty acid residues that abound in neutral fats. $R_3$ is primarily either the choline [$HOCH_2CH_2N(CH_3)_3OH$] ester or ethanolamine ($HOCH_2CH_2NH_2$) ester of phosphoric acid ($H_3PO_4$).

The emulsifier adjuvant generally comprises a neutral triglyceride of various fatty acids including linolenic, oleic, palmitic, stearic and linoleic acids. Such neutral triglycerides are generally available from a wide range of natural sources, including safflower oil and soybean oil. When the emulsifying adjuvant of the present invention comprises a 50/50 mixture of safflower oil and soybean oil, then the fatty acid components comprise approximately 65.8% linolenic acid, 17.7% oleic acid, 8.8% palmitic acid, 3.4% stearicacid and 4.2% linolenic acid. A typical triglyceride emulsion source is Liposyn®II 10% and 20% emulsions available from Abbott Laboratories, North Chicago, Ill. which contain 5–10% safflower oil, 5–10% soybean oil, 1.2% egg phosphatides, 2.5% glycerin and sodium chloride to adjust pH to 8–8.3.

The emulsion according to the present invention is preferably isotonic, containing an appropriate amount of sodium chloride or other electrolytes, including components in Ringer's solution or lactated Ringer's solution. Additionally, glycerine is present in an amount of approximately 2.5%.

Albumin, such as bovine serum albumin can be added to the present emulsions in an amount of 0.2 to 2.0 weight percent, preferably 1.0 weight percent to act as an oncotic agent for better control of emulsion particle and to avoid adverse effects of the emulsion on muscle cells of the heart of a mammal which is administered the emulsion.

The emulsion of fluorochemical compound according to the present invention contains particles of the fluorocompound having a size less than 0.1 microns and a mean particle size of about 0.15 microns. These fluorochemical particles are in stable emulsion in an autoclaved sterile aqueous system for periods of time exceeding 10 weeks at room temperature.

The concentration ranges for the subject perfluorochemical emulsions of the present invention are set forth below:

(A) Perfluorochemical: approximately 10–50 wt/vol percent;
(B) Liposyn® II 10% or 20% emulsion: 50–95 volume percent, and
(C) Water: 0.0–40 volume percent (additional water beyond that present in the Liposyn® II emulsions)

The perfluorochemical emulsion is prepared according to the following examples setting forth the emulsification of the above-identified components.

The process used to create the emulsion consists of the following steps:

1. A Microfluidizer apparatus is alcohol (ethanol) sterilized by passing 250 ml of a 75 vol% alcohol/water solution through the system for 10 minutes at 10,000 psi back pressure. All components that are removable were steam sterilized at 121° C. for 15 minuts in an autoclave. All water, perfluorochemical and associated glassware are steam sterilized. Liposyn® II emulsion was used "as received" from Abbott Labs as a sterile injectable nutrient fat emulsion.

2. Liposyn II (10 wt% or 20 wt%) and a perfluorochemical are combined together into the feed tube of the Microfluidizer. The reaction zone of the Microfluidizer sits on a base and resides within a tray. The tray is filed with crushed ice (0°–4° C.) to cool the reaction zone during microfluidization. The need for cooling is necessary because the process develops heat at the instant of processing. Such cooling reduces vapor loss of perfluorochemical and denaturing of the emulsifier. An additional heat exchanger was installed to the "outlet" line of the Microfluidizer to reduce the temperature of the partially prepared emulsion and allow continuous recycle. Crushed ice is used to affect the cooling of the flowing stream. Once the cooling configuration is in place, the master air pump is started and pressure is built-up to read between 13,000 and 15,000 psi on the supplied pressure gauge. Liquids are recycled through the unit for five (5) minutes. Such cycling represents 40–45 complete passes through the reaction zone. After the sample is processed it is collected and cooled to 20° C. prior to storage (4° C.) or analysis.

EXAMPLE I (9395-18-1)

Thirty (30) grams of perfluorodecalin (PF-decalin) and 85ml of Liposyn II (10%) were mixed together and allowed to cool to 20° C. prior to processing. The method used is that stated above. During processing the recycle stream of the fluids reached a measured temperature of 82° C. At withdrawal the processed fluid was 50° C. This fluid was captured and cooled to 20° C. Total processing pressure was 13,500 psi for five minutes. The resulting emulsion was stable (no creaming/separation) after 25 days. The emulsion was a 30 wt/vol% concentration of PF-decalin.

EXAMPLE II (8469-58-3)

Perfluoroperhydrophenanthrene (48 grams) was combined with 72 grams of Liposyn ® II 10% emulsion at 4° C. in the Microfluidizer apparatus. The process used was identical to that described in Example I.

The resulting emulsion had a particle size distribution of 0.09–0.15 microns. Oxygen solubility was 11 ml/100 ml of emulsion. The pH was 5.8 and the free fluoride concentration was <0.2 ppm. The surface tension was 37 dynes/cm. Perfluoroperhydrophenanthrene was 50 wt/vol% at 25° C. in this example. This emulsion remained stable for more than 90 days at 4° C.

EXAMPLE III (8469-41-1)

Eighty grams of perfluorodecalin was combined with 320 grams of Liposyn ® II/10% emulsion at 4° C. in the Microfluidizer apparatus using the process described in Example I.

The resulting emulsion had a pH or 7.3, surface tension of 57 dynes/cm, less than 0.2 ppm free fluoride and contained 6 ml oxygen per 100 ml of emulsion.

This emulsion was used to sustain an isolated rabbit heart by 100% blood exchange using 95% $O_2$ and 5% $CO_2$. The emulsion was diluted 1:1 with Krebs salts. The heart continued to function 40 minutes without exhibiting undue work output.

EXAMPLE IV (9395-13-1)

Fifty (60) grams of PF-decalin and 90ml of Liposyn II (10%) were combined and processed as described above. After 24 hours, 0.5–0.75 grams of PF-decalin were observed not to be emulsified. This emulsion is considered to be unstable at 50 wt/vol% PF-decalin.

EXAMPLE V (9395-18-2)

Sixty (72) grams of PF-decalin and 84ml of Liposyn II (10%) were combined and processed as described above. After 24 hours 1-2 grams of PF-decalin remained at the bottom of the sample. After 72 hours 5-9 grams of PF-decalin were observed at the bottom of the sample. This sample underwent "creaming" or separation of the oil from the bulk water phase. The emulsion attempted was to be a 60 wt/vol% PF-decalin emulsion in Liposyn II. This emulsion is considered unstable.

EXAMPLE VI (9395-18-3)

Eighty-seven (87) grams of PF-decalin and 80ml of Liposyn II (10%) combined and processed as described above. The system did not form a 70 wt/vol % emulsion. The process fluid reached a temperature of 86° C. This combination of PF-decalin and Liposyn II (10%) did not form an emulsion under these process conditions.

EXAMPLE VII (9395-21-3)

A 50 wt/vol % PF-decalin in Liposyn II (20%), using the method described above was made with the specific characteristics described below.

60.00 grams PF-decalin=30 ml
Initial temperature=17° C.
90.00 grams Liposyn (20%)=90 ml
Max. Process temperature=79° C.
Withdrawal temperature=46° C.

After five minutes process time, an emulsion was formed. After 19 days, emulsion was still stable.

EXAMPLE VIII (9395-21-2)

A 60 wt/vol % PF-decalin in Liposyn II (20%) using the method described above with the specific characteristics described below was attempted.

72.00 grams PF-decalin=36 ml
Initial temperature=18° C.
84.00 grams Liposyn (20%)=84 ml
Max. process temperature=84° C.
Withdrawal temperature=52° C.

After five minutes process time, an emulsion was formed. After fifteen hours, ½ grams of PF-decalin had fallen out of suspension. This emulsion is considered unstable.

EXAMPLE IX (9395-21-1)

A 70 wt/vol % PF-decalin in Liposyn II (20%) using the method described above with the specific characteristics described below was attempted.

90.00 grams PF-decalin=45ml
Initial temperature=18° C.
83.00 grams Liposyn (20%)=83ml
Max. process temperature=75° C.
Withdrawal temperature=48° C.

No emulsion formed after five minutes. After an additional five minutes an emulsion still did not form. This mixture is considered to fail as an appropriate emulsion.

EXAMPLE X

A 20 weight/volume percent emulsion of perfluorodecalin in Liposyn®II emulsion was prepared for injection into rabbits to demonstrate utility and lack of toxicity. Four rabbits (approximately 3000 grams) were administered 0.125 ml/Kg Innovar-vet, an analgesic/sedative drug subcutaneously 20 minutes prior to the procedure. With regard to three of the rabbits, when the animal was stable (20+ minutes after injection) 30-50 ml of whole blood was removed through the central ear artery and infusion of an equal volume of the perfluorodecalin—Liposyn® II emulsion was made. One animal was administered 20 ml of the Lyposyn II emulsion directly without any blood removed. The total blood/emulsion replacement ranged from 14-24 vol% of the animal. After 30 days, no overt toxicity was observed based upon gross behavioral or physiological symptoms. This example demonstrates the utility and nontoxic nature of the emulsions of the present invention.

The perfluorochemical emulsions of the present invention contain very fine particle sizes below that previously generally recorded in the prior art, which particles do not aggregate into coarse particles during normal storage of the emulsion for considerable periods of time. Accordingly, the perfluorochemical emulsions can be administered to mammals without harm to tissue due to the aggregation of particles. Furthermore, the perfluorochemical compounds used in the present invention are easily excreted through respiration when administered in the form of an emulsion as a blood substitute and minimal or no accumulation thereof in the liver or spleen has been observed. The perfluorochemical emulsion of the present invention can be administered intravenously to animals or patients suffering from bleeding or blood loss when accompanied with containment of the animal or patient under an increased oxygen content atmosphere. Besides the utility of blood substitution for mammals, the emulsions of the present invention can be used as perfusate for the preservation of internal organs, such as in procedures dictated by organ transplants or they can be used in cancer therapy.

Accordingly, the emulsions of the present invention can be used in a method of enhancing the transport of oxygen through the vascular system and into the tissue of mammals which comprises administering a volumetric amount of a perfluorochemical emulsion to said mammal sufficient to maintain the total vascular volume of said mammal and subjecting the respiratory function of the mammal to elevated concentrations of oxygen above atmospheric concentrations wherein said emulsion comprises approximately 10 to 50 weight/volume % of a perfluorochemical, approximately 0.5 up to 7 weight % of a phospholipid which emulsifies said perfluorochemical, approximately 5-30 weight % of a triglyceride of fatty acids, and the remainder of an aqueous medium.

Additionally, the emulsions of the present invention can be used in a method of preserving internal organs outside the body which comprises perfusing the same with a preoxygenated perfluorochemical emulsion comprising approximately 10 to 50 weight/volume % of a perfluorochemical, approximately 0.5 up to 7 weight % of a phospholipid which emulsifies said perfluorochemical, approximately 5-30 weight % of a triglyceride of fatty acids, and the remainder of an aqueous medium.

Finally, the emulsions of the present invention are produced by a method for preparing a stable aqueous emulsion of a perfluorochemical in a perfluorochemical concentration range of approximately 10–50 wt/vol% wherein an aqueous emulsifier is mixed with a perfluorochemical to result in a final aqueous perfluorochemical emulsion havig a perfluorochemical concentration in the range of 10 to 50 wt/vol% the improvement comprising using a perfluorochemical that is prepared by an initial fluorination of a chemical in the presence of cobalt trifluoride and subsequent complete fluorination of said chemical in the presence of elemental fluorine.

The perfluorochemical emulsions of the present invention are unique in that they provide previously unobtainable stability of perfluorochemical in an aqueous emulsion. Particularly by using triglycerides to emulsify the preferred perfluorochemical, namely perfluorodecalin, the present invention overcomes the specific problem of stable emulsification of perfluorodecalin documented in the prior art. For instance, Edward M. Levine and Alan E. Friedman describe in their paper "Artificial Blood on the Laboratory Horizon" published in LAB WORLD, October 1980 at page 56, that;

"The most extensively studied perfluorochemicals have been perfluorotributylamine and perfluorodecalin. Perfluorotributylamine forms extremely stable emulsions; however, it remains in the body for extensive periods. Perfluorodecalin leaves the body in 50 hours but is difficult to emulsify. Also, emulsions containing perfluorodecalin must be stored frozen, since they have a very limited stability at room temperature."

These prior art problems of emulsifying perfluorodecalin were further documented by Jean G. Reiss in his article "Reassessment of Criteria for the Selection of Perfluorochemicals for Second-Generation Blood Substitutes: Analysis of Structure/Property Relationships", published in ARTIFICIAL ORGANS, 8(1):44–56 Raven Press, New York in 1984, wherein it is stated;

"The tenacious efforts of the late Dr. Ryoichi Naito led, in 1978, to the development by The Green Cross Corporation (Osaka, Japan) of the first and still the only commercially available standard emulsion of perfluorochemicals (F-chemicals =highly fluorinated organic materials) suitable for research and clinical testing as a blood substitute - Fluosol-DA (1,2). The advent of Fluosol-DA was therefore an essential milestone in the progress of research in this field. It permitted the first clinical tests of an F-chemical-based blood substitute, and at the end of 1982, >500 patients, mainly in Japan and in the United States, had received Fluosol-DA. For recent reviews and symposia on F-chemical-based blood substitutes, see references 3-12.

In spite of its merits, not the least of which is its very existence, which permitted numerous research groups to progress, this "first-generation" preparation should be considered as only a first draft. Among its imperfections are that it is based on two oxygen carriers, F-decalin (70%) and F-tripropylamine (30%), with widely different characteristics: the latter carrier having an overlong half-retention time in the organism, $t_\frac{1}{2} = \sim 65$ days compared with 6 days for the former. Further, these F-chemicals contain several percent impurities. Still another problem is the limited storage stability of the emulsion, which makes it necessary to transport and store it in the frozen state. The use of a dual fluorocarbon carrier system was devised as a makeshift solution to circumvent the failure to achieve stable emulsions of F-decalin by the addition of F-tripropylamine, but at the expense of the much longer retention of the latter in the organs."

This difficulty in emulsifying and retaining stability of any appreciable amount of perfluorodecalin in a biocompatible emulsion was further alluded to by Henry Sloviter in U.S. Pat. No. 4,397,870 wherein he used large (7–9%) amounts of lecithin to emulsify perfluorodecalin in an aqueous phase and then taught that after administration of the emulsion to a patient, additional administrations of lecithin would be necessary to maintain the perfluorodecalin in emulsion in the bloodstream.

In contrast, the present invention uses only 0.5 up to 7 weight percent of a phospholipid (lecithin) and, by using triglycerides in the recited amount, has successfully overcome the difficulties of the prior art by producing long term-stable, physiologically acceptable, aqueous emulsions of perfluorochemicals and particular perfluorodecalin. Although the inventor does not wish to be held to any particular theory concerning the success of these emulsions, it is believed that the triglyceride constitutes an interface between the perfluorochemical particle and the emulsifier comprising the micelle in the aqueous continuous phase of the emulsion. By existing at the interface of the perfluorochemical and the emulsifier, the triglyceride which is more polar than mono- or diglycerides provides greater stability for the non-polar characteristics of the perfluorochemical and the polar characteristics of the continuous aqueous phase. This enhanced emulsifying capability of the triglycerides is exhibited by the stable emulsions demonstrated in the present examples which provides perfluorochemical emulsions having demonstrated long term stability.

Although the present invention has been described in accordance with several preferred embodiments, the scope of this invention should not be limited to such specific embodiments, but rather should be ascertained from the claims which follow:

I claim:

1. A stable aqueous emulsion of a perfluorochemical comprising approximately 10–50 weight/volume % perfluorochemical, approximately 0.5 up to 7 weight % of a phospholipid which emulsifies said perfluorochemical, approximately 5–30 weight % of a triglyceride of fatty acids as an emulsifier adjuvant, and the remainder of an aqueous medium.

2. The emulsion of claim 1 wherein the perfluorochemical is selected from the group consisting of perfluoroalkylcyclohexane having 3 to 5 carbon atoms in the alkyl radical, perfluorodecalin or perfluoromethyldecalin.

3. The emulsion of claim 1 wherein the perfluorochemical is perfluorodecalin.

4. The emulsion of claim 1 wherein the perfluorochemical is present in the range of 20 to 40 weight/volume %.

5. The emulsion of claim 1 wherein the phospholipid is an egg phosphatide.

6. The emulsion of claim 1 wherein the phospholipid is present in a range of 1-2 weight percent.

7. The emulsion of claim 1 wherein the triglyceride emulsifier adjuvant of of fatty acids is selected from the group consisting of safflower oil, soybean oil or mixtures thereof.

8. The emulsion of claim 1 wherein the triglyceride emulsifier adjuvant of of fatty acids is present in the range of 10 to 20 weight %.

9. The emulsion of claim 1 including an albumin component.

10. A stable emulsion in a physiologically acceptable aqueous medium of an oxygen-transferable saturated perfluorodecalin having essentially no detectable hydrogen or olefinic character and a mean particle size of about 0.15 microns which comprises said perfluorodecalin in a concentration of 10 to 50 weight/volume %, a phospholipid as an emulsifier in a concentration of approximately 1.2 weight %, at least one triglyceride of fatty acids as an emulsifier adjuvant in a concentration of 10 to 20 weight % wherein the fatty acids have 16 to 18 carbon atoms, and glycerin in an amount of approximately 2.5 weight %, said emulsion being suitable for use as a blood substitute.

11. A method of enhancing the transport of oxygen through the vascular system and into the tissue of mammals which comprises administering a volumetric amount of a perfluorochemical emulsion to said mammal sufficient to maintain the total vascular volume of said mammal and subjecting the respiratory function of the mammal to elevated concentrations of oxygen above atmospheric concentrations wherein said emulsion comprises approximately 10 to 50 weight/volume % of a perfluorochemical, approximately 0.5 up to 7 weight % of a phospholipid which emulsifies said perfluorochemical, approximately 5–30 weight % of a triglyceride of fatty acids as an emulsifier adjuvant, and the remainder of an aqueous medium.

12. A method of preserving internal organs outside the body which comprises perfusing the same with a preoxygenated perfluorochemical emulsion comprising approximately 10 to 50 weight/volume % of a perfluorochemical, approximately 0.5 up to 7 weight % of a phospholipid which emulsifies said perfluorochemical, approximately 5–30 weight % of a triglyceride of fatty acids as an emulsifier adjuvant, and the remainder of an aqueous medium.

13. In a method for preparing a stable aqueous emulsion of a perfluorochemical in a perfluorochemical concentration range of approximately 10–50 wt/vol% wherein an aqueous emulsifier is mixed with a perfluorochemical to result in a final aqueous perfluorochemical emulsion having a perfluorochemical concentration in the range of 10 to 50 wt/vol% the improvement comprising using a perfluorochemical that is prepared by an initial fluorination of a chemical in the presence of cobalt trifluoride and subsequent complete fluorination of said chemical in the presence of elemental fluorine.

14. A stable aqueous emulsion of a perfluorochemical comprising approximately 10–50 weight/volume % perfluorochemical, approximately 0.5 up to 7 weight % of a phospholipid which emulsifies said perfluorochemical, approximately 5–30 weight % of a triglyceride of fatty acids as an emulsifying adjuvant comprising an approximately 50/50 mixture of safflower oil and soybean oil having a fatty acid composition of approximately 65.8% linoleic acid, 17.7% oleic acid, 8.8% palmitic acid, 3.4% stearic acid and 4.2% linolenic acid, and the remainder of an aqueous medium.

* * * * *